US010170203B1

(12) United States Patent
Blechman

(10) Patent No.: US 10,170,203 B1
(45) Date of Patent: Jan. 1, 2019

(54) METHOD AND SOFTWARE FOR A WEB-BASED PLATFORM OF COMPREHENSIVE PERSONAL HEALTH RECORDS THAT ENFORCES INDIVIDUALIZED PATIENT HIERARCHIES OF USER PERMISSIONS AND DETECTS GAPS IN PATIENT CARE

(75) Inventor: Elaine A Blechman, Boulder, CO (US)

(73) Assignee: PROSOCIAL APPLICATIONS, INC., Boulder, CO (US)

( * ) Notice: Subject to any disclaimer, the term of this patent is extended or adjusted under 35 U.S.C. 154(b) by 207 days.

(21) Appl. No.: 13/418,768

(22) Filed: Mar. 13, 2012

Related U.S. Application Data

(63) Continuation-in-part of application No. 12/589,378, filed on Oct. 22, 2009, which is a continuation-in-part of application No. 10/853,488, filed on May 25, 2004, now abandoned, which is a continuation of application No. 10/431,845, filed on May 8, 2003, now abandoned, which is a continuation of application No. 10/210,127, filed on Aug. 1, 2002, now abandoned.

(51) Int. Cl.
*G06F 19/00* (2018.01)
*G16H 10/60* (2018.01)
*G06Q 50/22* (2018.01)

(52) U.S. Cl.
CPC ............ *G16H 10/60* (2018.01); *G06Q 50/22* (2013.01)

(58) Field of Classification Search
CPC ........ G06Q 50/22; G06Q 50/24; G06Q 50/18; G06Q 10/06; G06Q 40/02; G16H 10/60
USPC .......................................................... 705/3
See application file for complete search history.

(56) References Cited

U.S. PATENT DOCUMENTS

| | | | |
|---|---|---|---|
| 6,023,762 | A | 2/2000 | Dean et al. |
| 6,024,699 | A | 2/2000 | Surwit et al. |
| 6,612,985 | B2 | 9/2003 | Eiffert et al. |
| 6,735,551 | B2 | 5/2004 | Voegeli et al. |

(Continued)

OTHER PUBLICATIONS

Hall, Jon. Red Hat® Linux® for Dummies®, IDG Books Worldwide, Inc. Foster City, CA, 2000.

*Primary Examiner* — Hiep V Nguyen
(74) *Attorney, Agent, or Firm* — Holzer Patel Drennan

(57) ABSTRACT

The invention is a method for an unbound, interoperable, web-based software platform, comprising comprehensive personal health records (PHRs) of patients, enforcing individualized patient hierarchies of user permissions when creating, managing, accessing, updating, exchanging, and consolidating information, offering unique capabilities for detecting gaps in care, coordinating care, and prompting provider compliance with practice guidelines and government regulations.

The Platform comprises four encrypted, firewall protected layers that together support Platform capabilities. First, the Platform is distinguished from conventional EHRs and tethered PHRs by individualized patient hierarchies of user permissions in the application layer, controlling disclosures of data to authorized users. Second, the Platform is distinguished by scanning of data and application layers for gaps in patient care and alerting relevant users. Third, the Platform is distinguished by tagging data with individualized patient hierarchies of user permissions, filtering data disclosures to authorized users and impeding data handoffs to unauthorized users.

16 Claims, 9 Drawing Sheets

(56) References Cited

U.S. PATENT DOCUMENTS

| | | | |
|---|---|---|---|
| 7,016,877 | B1 | 3/2006 | Steele et al. |
| 7,716,069 | B2 | 5/2010 | Ulrich et al. |
| 7,849,400 | B2 | 12/2010 | Ritter et al. |
| 7,856,366 | B2 | 12/2010 | Dettinger et al. |
| 2002/0004727 | A1* | 1/2002 | Knaus et al. ............... 705/3 |
| 2002/0010679 | A1* | 1/2002 | Felsher ............... 705/51 |
| 2002/0013716 | A1 | 1/2002 | Dunham |
| 2002/0032583 | A1 | 3/2002 | Joao |
| 2002/0099568 | A1 | 7/2002 | Turner et al. |
| 2002/0099598 | A1 | 7/2002 | Eicher, Jr. et al. |
| 2002/0165733 | A1 | 11/2002 | Pulkkinen et al. |
| 2002/0184527 | A1* | 12/2002 | Chun et al. ............... 713/201 |
| 2003/0140043 | A1 | 7/2003 | Hotchkiss et al. |
| 2003/0236682 | A1 | 12/2003 | Heyer |
| 2008/0059250 | A1 | 3/2008 | Joao |

* cited by examiner

METHOD AND SOFTWARE FOR A WEB-BASED PLATFORM OF COMPREHENSIVE PERSONAL HEALTH RECORDS THAT ENFORCES INDIVIDUALIZED PATIENT HIERARCHIES OF USER PERMISSIONS AND DETECTS GAPS IN PATIENT CARE

This application is a continuation-in-part of pending application Ser. No. 12/589,378 filed Oct. 22, 2009 which is a continuation-in-part of pending application Ser. No. 10/853,488 filed May 25, 2004 and, in turn, is a continuation of Ser. No. 10/431,845 filed May 8, 2003 which is a continuation of Ser. No. 10/210,127 filed Aug. 1, 2002, now abandoned. The disclosure of each of the foregoing applications is herein incorporated by reference.

FIELD OF THE INVENTION

In the fragmented U.S. health care ecosystem, patients with chronic illnesses and disabilities usually receive services from many health care providers, who all maintain their own insular electronic health record systems (EHRs). Fragmented care delivery and record keeping result in gaps in patient care, which reduce the safety and quality of care and increase costs. Gaps result when one or more providers have insufficient information about a particular patient's clinical status or about the clinical guidelines or government regulations that apply given the clinical status of a particular patient. For example, Dr. A decides that Patient X has an allergy to penicillin; Dr. B prescribes penicillin for Patient X. Dr. C orders an MRI for Patient X; soon after, Dr. D orders the same MRI. Dr. E refers Patient X to a specialist, Dr. F; but Dr. F does not accept Medicare patients. Dr. G treats Patient X for pain, but offers no options for after-hours care except the local hospital's emergency department; Patient X is needlessly admitted to the hospital. Dr. H recommends daily physical activity, but Patient X does not comply. A vendor charges Medicare for durable medical equipment that Patient X never receives.

Providers maintain their own EHRs as legal documentation only for the services they provide to their patients and so each patient has partial health information in many EHRs. Providers cannot eliminate gaps in care of their patients merely by searching their own EHRs or by electronically exchanging patient information partial information (e.g., a discharge or a referral summary) with other providers.

Providers and their patients, particularly those with chronic conditions, need web-based comprehensive records drawn from multiple record sources as the basis for gap detection and resolution. Providers need convenient options for accessing comprehensive patient records through suitable provider interfaces or through their existing EHRs. Because each comprehensive record includes the totality of a patient's health information, each patient needs to establish an individualized hierarchy of permissions for access to the record, granting providers permissions suitable for the roles they play in patient care. These needs are filled by the present invention, an unbound, interoperable personal health record (PHR) software platform that consolidates information from the electronic health record systems (EHRs) of each patient's many providers, enforcing access consistent with individualized user permission hierarchies.

The present invention is directed to a method for an unbound, interoperable, web-based software platform (hereinafter the "Platform"), comprising comprehensive electronic personal health records (PHRs) of multiple patients, enforcing individualized patient hierarchies of user permissions when creating, managing, accessing, exchanging, and consolidating information in the PHRs of patients, thereby offering unique capabilities for detecting gaps in patient care and gaps in compliance with clinical guidelines and government regulations.

The Platform comprises four separately encrypted, firewall protected layers that interact with each other, giving rise to the Platform's capabilities. An infrastructure layer, defined as offering the basic structures needed for Platform operation, includes components such as programming logic, relational databases, authentication and cryptography. A data layer, defined as offering the application layer access to data stored in the infrastructure layer, includes data segments such as conditions, medications, allergies, procedures, recommendations and observations. An application layer, defined as offering business rules needed for communications within and between layers, includes embedded patient user permission hierarchies, public policies and evidence-based clinical and practice guidelines. A presentation/transport layer, defined as offering delivery and formatting of information to the application layer for further processing or display and decryption of data presented or transported to users, includes various user interfaces. Through the user interfaces of the presentation/transport layer, various users receive (are presented with) and send (initiate transport of) information from and to the application layers. User interfaces of the presentation/transport layer are available for patients, for providers without electronic health records (EHRs), for administrators, for researchers, for participants in health information exchange organizations and for health insurance payers. User interfaces accommodate web services, defined as a method of communication between two electronic devices over the web. User interfaces also offer users tools for automating data exchange between the personal health records (PHRs) of patients and the electronic health records (EHRs) of providers.

The Platform is distinguished from conventional EHRs and tethered patient portals in these ways. First, individualized patient hierarchies of user permissions are embedded in the Platform application layer, controlling disclosures of data to authenticated patient and provider users through the presentation/transport layer. Second, the Platform continuously scans data and application layers for gaps in patient care and in regulatory compliance and escalates alerts about gaps to patients and providers with suitable permissions. Third, the Platform permanently tags data elements with information about individualized patient hierarchies of user permissions, selectively filtering data disclosed to authorized users and impeding handoffs of data by authorized to unauthorized users.

BACKGROUND OF THE INVENTION

Fragmented care. About 20 percent of US adults, who receive independent services from two or more providers for multiple chronic physical, mental and substance abuse conditions, account for nearly 50 percent of US health care spending. Fragmented care of patients with five or more chronic conditions accounts for more than 90 percent of Medicare spending. Fragmented care is so unsatisfactory, dangerous, ineffective, and costly that it threatens the US economy and the national debt. Paradoxically, at all income levels in the US, fragmented care is the rule and integrated care the exception. As a patient's frequency of co-occurring chronic conditions increases, so does fragmentation of the patient's care across multiple providers. In a single year, the typical Medicare beneficiary sees two primary care physicians and five specialists in four different practices, with no one provider accountable for the safety, quality and costs of the patient's care.

Gaps in patient care, for the purposes of this patent application are defined to mean poorly coordinated care of patients, resulting in needless danger and expense. For example, Dr. A prescribes penicillin for Patient X, even though Dr. B previously diagnosed Patient X as having an allergic reaction to penicillin. Or, Dr. C orders an MRI for Patient X, even though Dr. D ordered the same MRI one month ago. Or, Dr. E refers Patient X to Dr F for confirmation of a cancer diagnosis, but Dr. F's office refuses to schedule the appointment because Patient X is covered only by Medicaid.

Gaps in regulatory compliance are defined to mean misalignment of provider services with applicable regulations. For example, Dr. G is a Medicare provider covered by requirements for meaningful use of electronic health records but does not update Patient X's medication and allergy lists during an encounter for which he bills Medicare.

Electronic health records (EHRs). Conventional EHRs are defined as electronic versions of providers' medical record systems. Patients with many EHR-equipped providers, have many EHR records as well as opportunities for provider-to-provider misunderstandings, gaps in care, and diffusion of responsibility. Since 2001, the US has encouraged provider adoption of EHRs to make health care safer and more efficient. Despite the availability of incentives for meaningful use of EHRs to eligible professionals and hospitals from the Centers for Medicare and Medicaid Services (CMS), only a fraction of providers serving patients with chronic conditions are eligible for these incentives. Among those who are eligible, rates of EHR implementation are lowest among providers of care to chronically ill and disabled patients. The fragmented storage of patient data in unconnected paper files and EHRs exacerbates diffusion of responsibility for all patients, fostering gaps in care of the patients who frequently utilize health care services.

Personal health records (PHRs). PHRs are defined as electronic versions of patients' records of their own health information. Tethered PHRs (or patient portals) give patients partial online views of their information in the EHR of a practitioner, hospital or health insurance payer. Standalone PHRs reside on portable storage devices and require manual entry by patients of their own health information. The present invention involves a unique unbound, interoperable PHR Platfoi ii unlike tethered PHRs, not tethered to any one EHR, unlike standalone PHRs, capable of automatically consuming and integrating data from multiple EHR sources.

A personal health record (PHR) Platform is defined as a place to launch the programming logic so that the code will run consistently executing its intended capabilities described below.

Differentiating the PHR Platform from Conventional EHRs and Tethered PHRs

First, the Platform is distinguished from conventional EHRs and tethered PHRs by individualized patient hierarchies of user permissions embedded in the application layer, controlling disclosures of data to authenticated users through the presentation/transport layer. Users who properly identify themselves from web-connected and mobile devices (e.g., through login entries or tokens) are authenticated at the infrastructure layer by authorization records, matched with permissions in the application layer, and offered authorized disclosures of decrypted data through the presentation/transport layer. Firewalls and encryption prevent Platform access by authorized or unauthorized users beyond the presentation/transport layer. Patients or their delegates employ user interfaces in the presentation and transport layer (hereinafter "patient user interfaces") to authorize providers they trust (hereinafter "primary providers") with the highest level of user permissions including the capacity to authorize lesser permissions for other providers (hereinafter "secondary providers"), thereby establishing individualized patient hierarchies of user permissions for access to data in patient's PHRs.

Second, the Platform is distinguished by continuous scanning of data and application layers for gaps in patient care and by escalating alerts to users with suitable permissions. Programming logic in the infrastructure layer scans for gaps within and between data and application layers such as prescription of a drug to which a patient is allergic, or absence of results for a lab test for which the lab has been paid. Consistent with individualized patient hierarchies of user permissions, the presentation/transport layer pushes and escalates alerts to users' mobile devices, consistent with users' alert preferences, until several users confirm contributions to gap remediation.

Third, the Platform is distinguished by tagging of data elements with information about individualized patient hierarchies of user permissions, selectively filtering data disclosed to authorized users and impeding handoffs of data by authorized to unauthorized users. Programming logic in the infrastructure layer tags data elements stored in relational databases, identifying membership in data segments (such as physical health or mental health), associations with user permission hierarchies, data element sources and versions. Original and updated versions of data elements and their tags are stored permanently, subject to archiving from view in user interfaces but, barring patient requests, not to deletion. Programming logic relies on tags to assure that only permitted data (e.g., risk factors and physical health but not mental health or substance abuse) are disclosed to users through the presentation/transport layer. Embedded tags, akin to bar codes on physical objects, travel with data after export to authorized users, are difficult to remove and increase the risks and costs of improper handoffs and resale of patient data. Continuous auditing of user access to tagged data elements documents disclosures for patients, reducing overhead of providers associated with information exchange for referrals, transitions of care and care coordination.

Unique Advantages of the PHR Platform Compared to Conventional EHRs and Tethered PHRs The PHR Platform offers a unique advantage, compared to conventional EHRs and tethered PHRs, for cross-provider care coordination without violation of individualized patient hierarchies of user permissions. From the presentation/transport layer of the Platform, in accordance with individualized patient user permission hierarchies, users may enter and update patient data including conditions, referrals, encounters, medications, recommendations, adverse reactions, and care plans. Patients, family caregivers and multiple providers may update patients' PHRs simultaneously (without waiting for one user to logoff before another user can login) or sequentially; manually through patient and provider user interfaces or automatically through exchanges of continuity of care documents with electronic health record systems (EHRs) or through web services; in point-to-point exchanges of one patient's data or in batch exchanges of many patients' data. Programming logic in the infrastructure layer of the Platform uses tags to recognize and consolidate new with existing data elements, to share comprehensive data with authorized users when they choose to access the Platform, and to push alerts to user's mobile devices, in accordance with individualized patient user permission hierarchies, about gaps in care that may needlessly endanger patient safety or waste resources. For example, an alert may be pushed out and escalated when a community-based provider fails to schedule an encounter within a week of a patient's discharge from hospital to his care. Or, an alert may be pushed out when a consultant orders tests duplicating tests ordered within the past month, the results of which are available in the patient's PHR. Alerts are escalated in accordance with the patient hierarchy of user permissions until the primary provider indicates remediation of the gap.

The PHR Platform offers a unique advantage, compared to conventional EHRs and tethered PHRs, for provider compliance with practice guidelines and government regulations without violation of individualized patient hierarchies of user permissions. Programming logic in the infrastructure layers uses tags on data elements to match patient data with practice guidelines and government regulations and to prompt providers for compliance in accordance with individualized patient user permission hierarchies. Providers receive prompts through the provider user interface in the presentation/transport layer, when for example, a medication list has not been updated as per Centers for Medicare and Medicaid Services (CMS) meaningful use requirements or when a patient over age 65 has not received a flu shot per CMS Clinical Quality Measure requirements. Continuous auditing in the infrastructure layer documents compliance with practice and regulatory requirements together with exceptions that providers enter to justify non-compliance.

In comparison to the present invention, in conventional EHRs patients have no way to register preferences for access to their EHR records by individuals in provider organizations or to audit such access. Conventional EHRs give providers no way to control, document or inform patients about the exchange of patient information outside their organizations as when they refer patients to consultants, transfer patients to other providers, or coordinate care with the patient's other current providers. To minimize liabilities associated with privacy breaches, providers equipped only with conventional EHRs minimize external information exchanges or place the burden on patients to convey information to other providers, inadvertently compromising the quality and safety of patient care.

Objectives.

The present invention is designed for use by patients, providers with and without EHRs, administrators, health information exchanges and health insurance payers as a means of optimizing care coordination and streamlining regulatory compliance without compromising the privacy preferences of patients.

SUMMARY OF THE INVENTION

The present invention is directed to a method for an unbound, interoperable, web-based software platform (hereinafter the "Platform"), comprising comprehensive electronic personal health records (PHRs) of multiple patients, enforcing individualized patient hierarchies of user permissions when creating, managing, accessing, exchanging, and consolidating information in the PHRs of patients, thereby offering unique capabilities for detecting gaps in patient care and gaps in compliance with clinical guidelines and government regulations.

The Platform comprises four separately encrypted, firewall protected layers that interact with each other, giving rise to the Platform's capabilities. First and foremost, the Platform is distinguished from conventional EHRs and tethered PHRs by individualized patient hierarchies of user permissions embedded in the application layer, controlling disclosures of data to authenticated users through the presentation/transport layer. Second, the Platform is distinguished by continuous scanning of data and application layers for gaps in patient care and by escalating alerts to users with suitable permissions. Third, the Platform is distinguished by tagging of data elements with information about individualized patient hierarchies of user permissions, selectively filtering data disclosed to authorized users and impeding handoffs of data by authorized to unauthorized users. The PHR Platform offers a unique advantage, compared to conventional EHRs and tethered PHRs, for cross-provider care coordination without violation of individualized patient hierarchies of user permissions. The PHR Platform also offers a unique advantage, compared to conventional EHRs and tethered PHRs, for provider compliance with practice guidelines and government regulations without violation of individualized patient hierarchies of user permissions. The present invention is designed for use by patients, providers with and without EHRs, administrators, health information exchanges and health insurance payers as a means of optimizing care coordination and streamlining regulatory compliance without compromising the privacy preferences of patients.

BRIEF DESCRIPTION OF THE DRAWINGS

Other features and advantages of the present invention will become apparent from the following detailed description of the preferred embodiment when read in conjunction with the following drawings of which:

FIG. 1 also shows that the PHR Platform is distinguished by individualized patient hierarchies of user permissions (ref#5) embedded in the application layer controlling disclosures of data to authenticated users through the presentation/transport layer.

DESCRIPTION OF THE PREFERRED EMBODIMENT

The present invention, illustrated in the following drawings, is directed to a method for an unbound, interoperable, web-based software platform, comprising comprehensive electronic personal health records (PHRs) of multiple patients, enforcing individualized patient hierarchies of user permissions when creating, managing, accessing, exchanging, and consolidating information in the PHRs of patients, thereby offering unique capabilities for detecting gaps in patient care and gaps in compliance with clinical guidelines and government regulations.

FIG. 1

Figure 1:
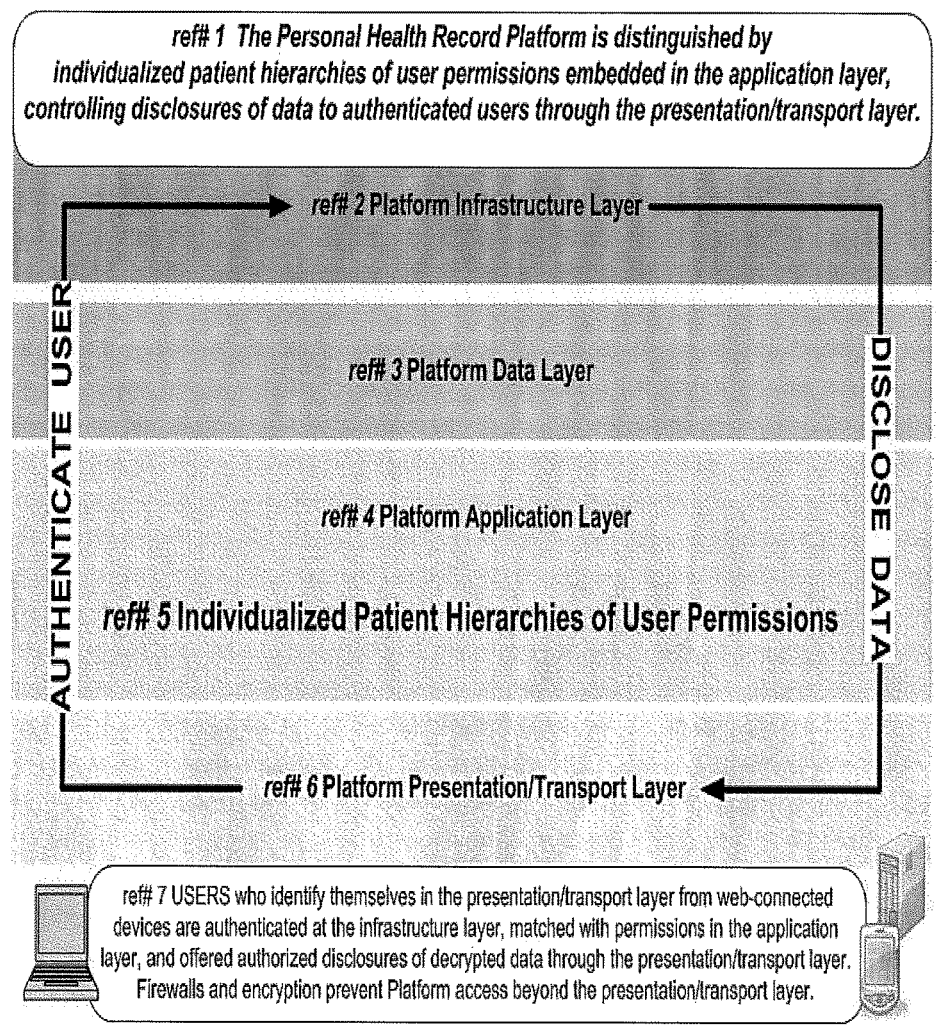
FIG. 1 shows the PHR Platform's four layers, infrastructure (ref#2), data (ref#3), application (ref#4), and presentation/transport (ref#5), which in interaction with each other give rise to the Platform's capabilities.

FIG. 1 shows that the Platform comprises four separately encrypted, firewall protected layers that interact with each other, giving rise to the Platform's capabilities, distinguished by individualized patient hierarchies of user permissions embedded in the application layer, controlling disclosures of data to authenticated users through the presentation/transport layer (ref#1). An infrastructure layer (ref#2), defined as offering the basic structures needed for Platform operation, includes components such as programming logic, relational databases, authentication and cryptography. A data layer, defined as offering the application layer access to data stored in the infrastructure layer, includes data segments such as conditions, medications, allergies, procedures, recommendations and observations (ref#3). An application layer, defined as offering business rules needed for communications within and between layers, includes embedded patient user permission hierarchies, public policies and evidence-based clinical and practice guidelines (ref#4). And, a presentation/transport layer, defined as offering delivery and formatting of information to the application layer for further processing or display and decryption of data presented or transported to users, includes user interfaces for patients, providers without EHRs, administrators, researchers, health information exchanges and health insurance payers; web services, defined as a method of communication between two electronic devices over the web; and, tools for data exchange between patient PHRs and provider EHRs. (ref#6).

In particular, FIG. 1 shows that the PHR Platform is distinguished from conventional EHRs and tethered PHRs by individualized patient hierarchies of user permissions embedded in the application layer (ref#5), controlling disclosures of data to authenticated users through the presentation/transport layer in the following way. Users who identify themselves in the presentation/transport layer from web-connected devices are authenticated at the infrastructure layer, matched with permissions in the application layer, and offered authorized disclosures of decrypted data through the presentation/layer. Firewalls and encryption prevent Program access by any user beyond the presentation/transport layer (ref#7).

FIG. 2.

Figure 2:
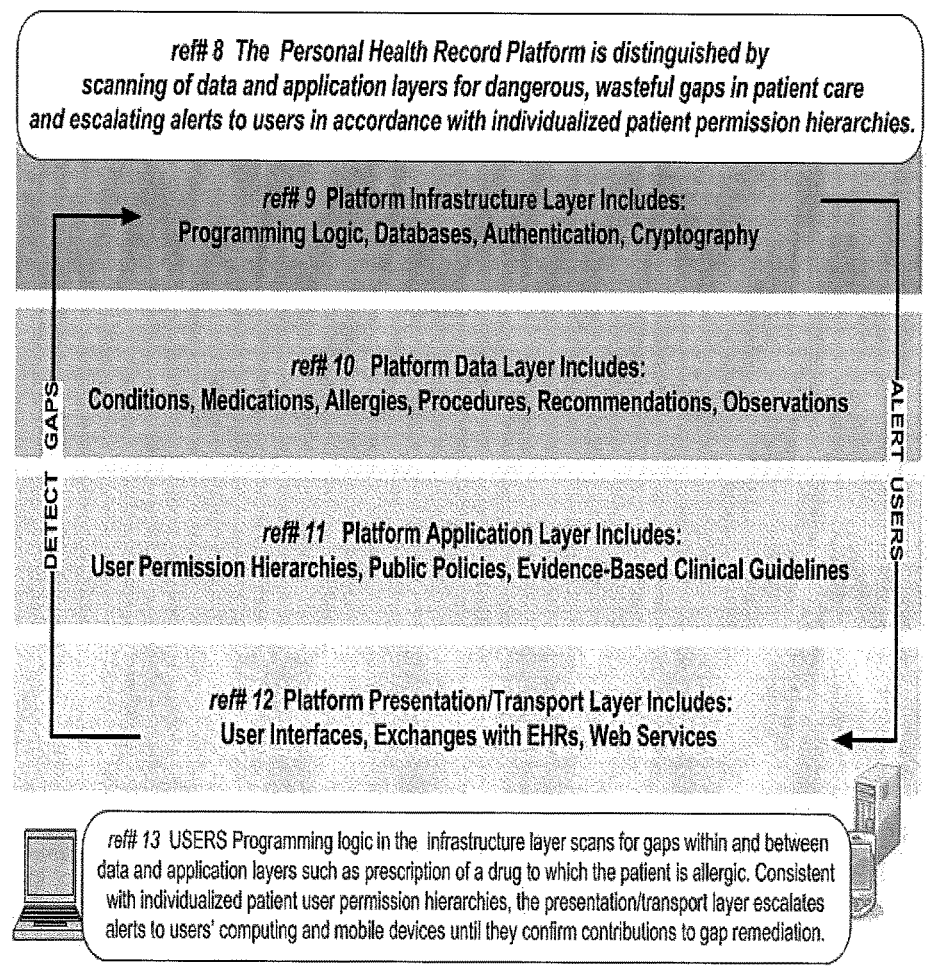
FIG. 2 shows that the PHR Platform is distinguished by scanning of data (ref#10) and application (ref#11) layers for gaps in patient care and escalating alerts to users with suitable permissions through the presentation/transport layer (ref#12).

FIG. 2 shows components of the PHR Platform infrastructure layer (programming logic, databases, authentication, and cryptography) (ref#9), of the data layer (conditions, medications, allergies, procedures, recommendations, and observations) (ref#10), of the application layer (user permission hierarchies, public policies, evidence-based clinical guidelines) (ref#11), and of the presentation/transport layer (user interfaces, tools for automating exchange of data in PHRs with electronic health records (EHRs), and webs services) (ref#12) related to detection of gaps in patient care, illustrating that interactions between Platform layers and within the components of each layer give rise to capabilities for detection of gaps in patient care and alerting of users. In particular, FIG. 2 shows that the PHR Platform is distinguished by scanning of data and application layers for gaps in patient care and escalating alerts to users with suitable permissions (ref#8). Programming logic in the infrastructure layer (ref#9) scans for gaps within and between data and application layers (ref#10, 11) such as prescription of a drug to which the patient is allergic or a diagnostic test that has been recommended but not completed. Consistent with individualized hierarchies of permissions, the presentation/transport layer (ref#13) sends and escalates alerts to users' computing devices, including mobile devices, indicating that a contraindicated drug has been prescribed, in the order established by the primary provider, until the primary provider confirms the gap has been addressed (e.g., patient told to discontinue contraindicated drug) (ref#13).

FIG. 3.

Figure 3:
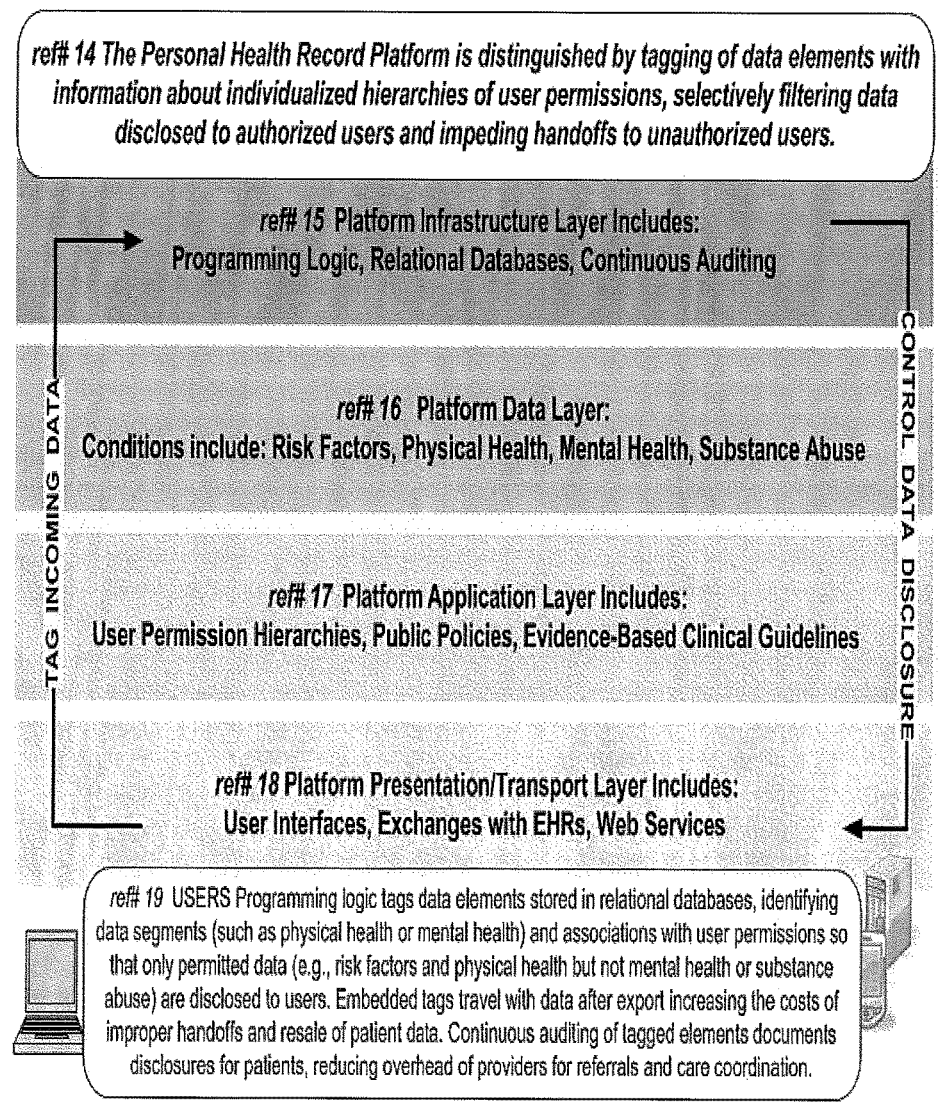
FIG. 3 shows the PHR Platform is distinguished by tagging of data elements stored in relational databases (ref#15) with information about individualized hierarchies of user permissions (ref#17), selective filtering data disclosed to authorized users through the presentation/transport layer (ref#18) and impeding handoffs to unauthorized users.

FIG. 3 shows components of the PHR Platform infrastructure layer (programming logic, relational databases, continuous auditing) (ref#15), of the data layer (risk factors, physical health, mental health and substance abuse conditions) (ref#16), of the application layer (user permission hierarchies, public policies, evidence-based clinical guidelines) (ref#17), and of the presentation/transport layer (user interfaces, tools for data exchange between patient PHRs and provider electronic health records (EHRs), and web services) (ref#18) related to tagging of data elements with information about individualized hierarchies of user permissions, illustrating that interactions between Platform layers and within the components of each layer give rise to capabilities for tagging incoming data and controlling data disclosures. In particular, FIG. 3 shows that the PHR Platform is distinguished by tagging of data elements (defined as the smallest meaningful units of data) with information about individualized hierarchies of user permissions, selectively filtering data disclosures to authorized users and impeding handoffs of data to unauthorized users (ref#14) via the presentation/transport layer. Programming logic tags data elements stored in relational databases, identifying data segments (such as physical health or mental health) and associations with user permissions so that only permitted data (e.g., risk factors and physical health but not mental health or substance abuse) are disclosed to users. Embedded tags travel with data after export increasing the costs of improper handoffs and resale of patient data. Based on continuous auditing of tagged elements, reports are available to patients about disclosures of their data, so that providers need not manually document such disclosures during referrals and care coordination (ref #19).

FIG. 4.

Figure 4:
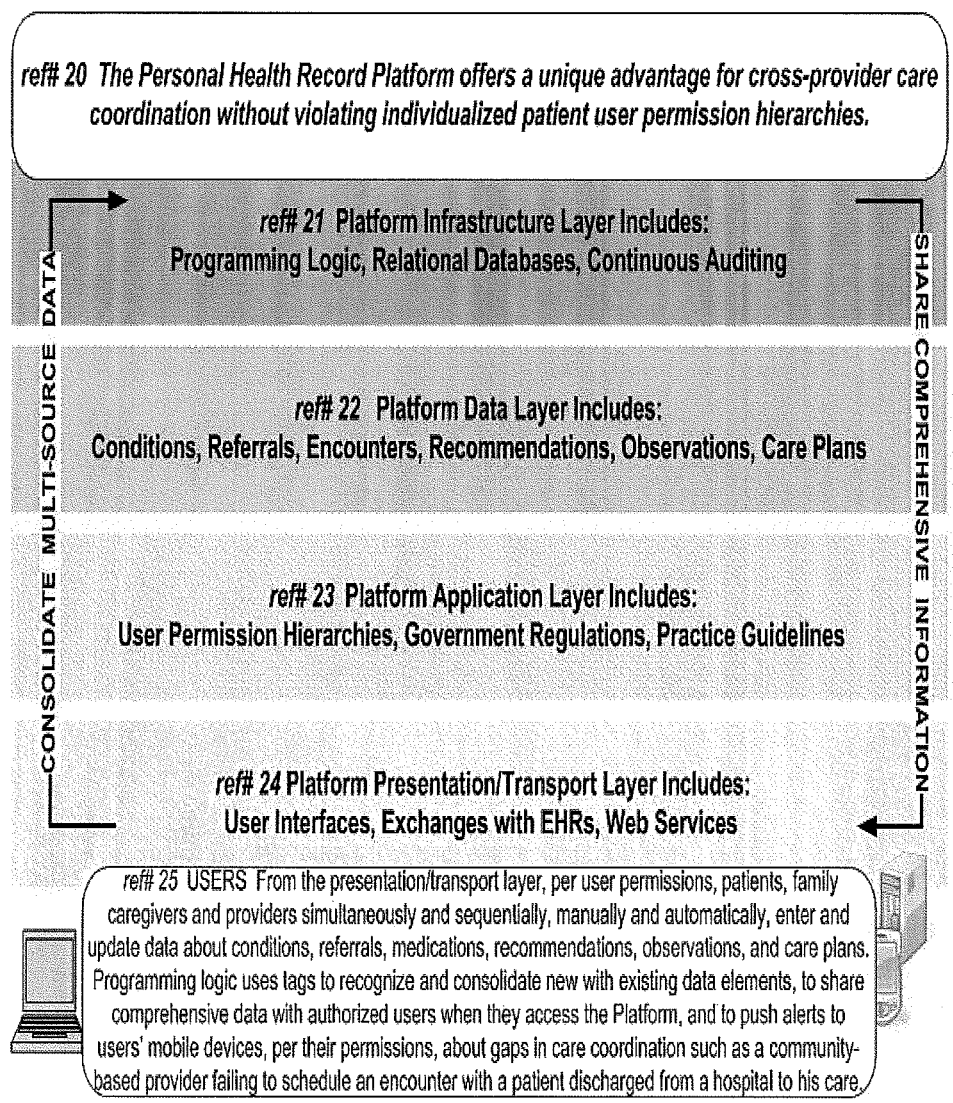
FIG. 4 shows the PHR Platform offers a unique advantage for cross-provider care coordination without violation of individualized patient hierarchies of user permissions by consolidating multi-source data through the infrastructure layer (ref#21) and sharing comprehensive information in accordance with user permission hierarchies (ref#23) through the presentation/transport layer (ref#24).

FIG. 4 shows components of the PHR Platform infrastructure layer (programming logic, relational databases, continuous auditing) (ref#21), of the data layer (conditions, referrals, encounters, recommendations, observations, care plans) (ref#22), of the application layer (user permission hierarchies, government regulations, practices guidelines) (ref#23), and of the presentation/transport layer (user interfaces, tools for data exchange between patient PHRs and provider electronic health records (EHRs), and web services) (ref#24) related to cross-provider care coordination without violation of individualized patient hierarchies of user permissions and illustrating that interactions between Platform layers and within the components of each layer give rise to capabilities for consolidating multi-source incoming data and sharing comprehensive outgoing data.

In particular, FIG. 4 shows that the PHR Platform offers a unique advantage, compared to conventional EHRs and tethered PHRs, for cross-provider care coordination without violation of individualized patient user permission hierarchies (ref#20). From the presentation/transport layer (ref#24), per user permissions (ref#23), patients, family caregivers and providers simultaneously and sequentially, manually and automatically, enter and update data about conditions, referrals, medications, recommendations, observations, and care plans (ref#22). Programming logic (ref#21) uses tags to recognize and consolidate new with existing data elements, to share comprehensive data with authorized users when they access the Platform, and to push alerts to users' computing devices, including mobile devices, per user permissions, about gaps in care such as a community-based provider failing to schedule an encounter with a patient discharged from a hospital to the provider's care (ref#25).

FIG. 5.

Figure 5:
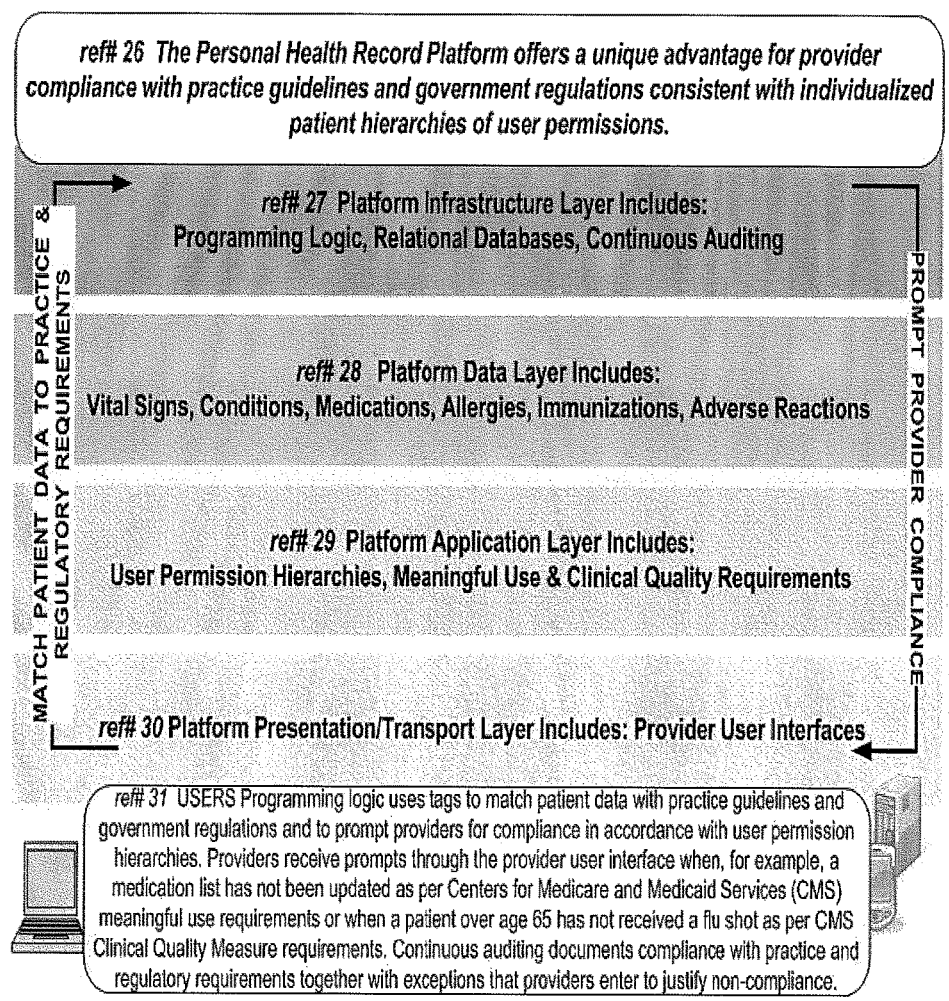
FIG. 5 shows the PHR Platform offers a unique advantage for provider compliance with practice guidelines and government regulations without compromise of patients privacy preferences by matching patient data to practice and regulatory requirements through the application layer (ref#29) and prompting provider compliance through the presentation/transport layer (ref#30).

FIG. 5 shows components of the infrastructure layer (programming logic, relational databases, continuous auditing) (ref#27), of the data layer (vital signs, conditions, medications, allergies, immunizations, adverse reactions) (ref#28), of the application layer (user permission hierarchies, meaningful use and clinical quality measure requirements) (ref#29), and of the presentation/transport layer (user interfaces, tools for data exchange between patient PHRs and provider electronic health records (EHRs), and web services) (ref#30) related to provider compliance with practice guidelines and government regulations without violation of individualized patient hierarchies of user permissions, and illustrating that interactions between Platform layers and within the components of each layer give rise to capabilities for matching incoming patient data to practice regulatory requirements and sending outgoing prompts to providers about compliance.

In particular, FIG. 5 shows that PHR Platform offers a unique advantage for provider compliance with practice guidelines and government regulations without violation of individualized patient hierarchies of user permissions (ref#26). Programming logic uses tags to match patient data with practice guidelines and government regulations and to prompt providers for compliance in accordance with user permission hierarchies. Providers receive prompts through the provider user interface (ref#30) when, for example, a medication list has not been updated as per Centers for Medicare and Medicaid Services (CMS) meaningful use requirements or when a patient over age 65 has not received a flu shot as per CMS Clinical Quality Measure requirements. Continuous auditing documents compliance with practice guidelines and regulations together with exceptions that providers enter to justify non-compliance.

FIG. 6.

Figure 6:
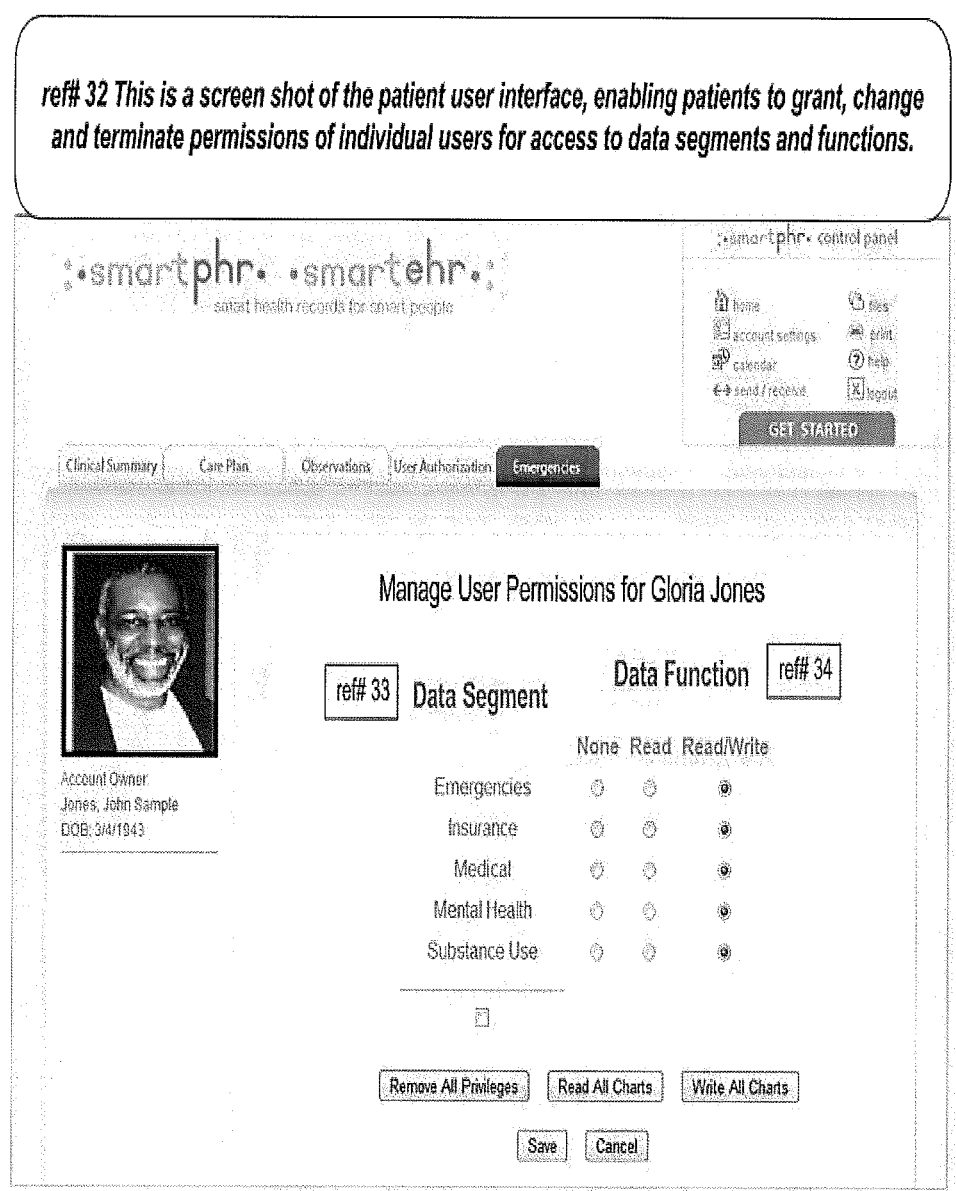
FIG. 6 is a screen shot of the patient user interface, enabling patients to grant, change and terminate permissions of individual users for access to data segments and functions.

FIG. 6 shows a screen shot (ref#32) of the patient user interface, enabling patients to grant, change and terminate permissions of individual users for access to data segments (ref#33) and functions (ref#34). Once a patient grants a primary provider the ability to authorize secondary providers with permissions less than theirs, primary providers access a provider interface that displays only permissions lesser than those of primary providers. From this interface, primary providers may select permissions by clicking on choices that confer permissions lesser than their own. No options are presented to primary providers for authorization of permissions equal to or greater than theirs. Authorization of secondary providers by primary providers is useful for clinical purposes including referrals, care transitions and care coordination,

FIG. 7.

Figure 7:
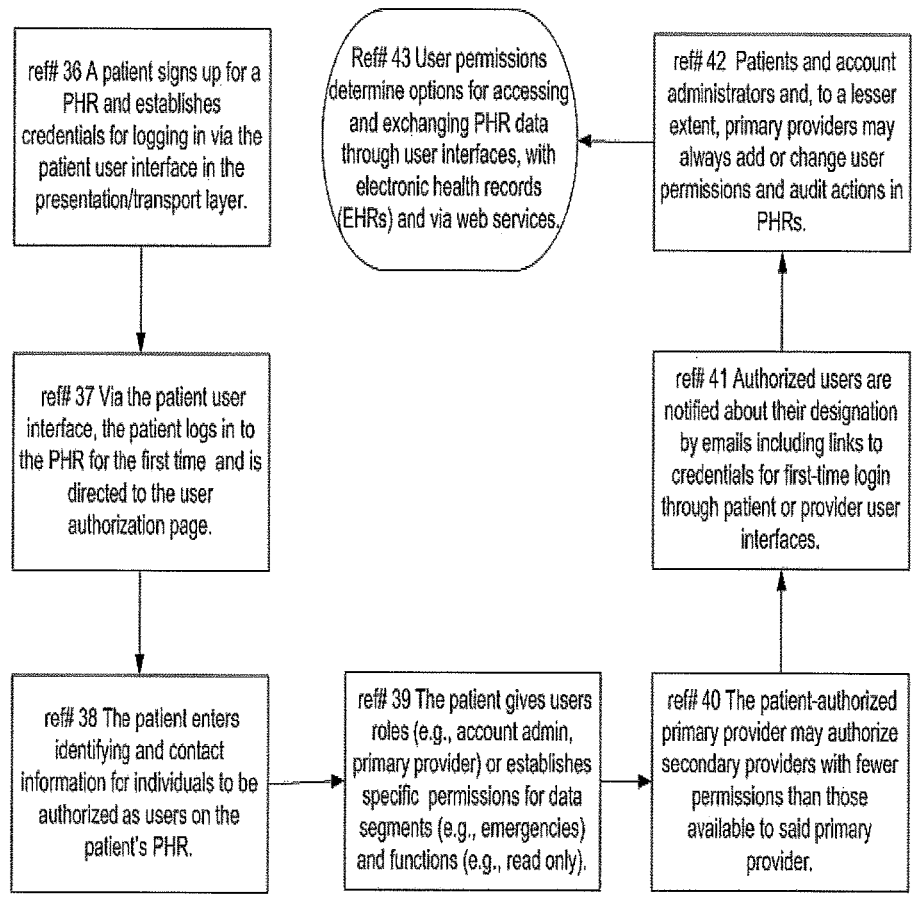
FIG. 7 is a block diagram showing how the PHR Platform creates, manages, accesses, and exchanges a personal health record (PHR) for one patient in accordance with the patient's individualized hierarchy of user permissions.
Figure 8:
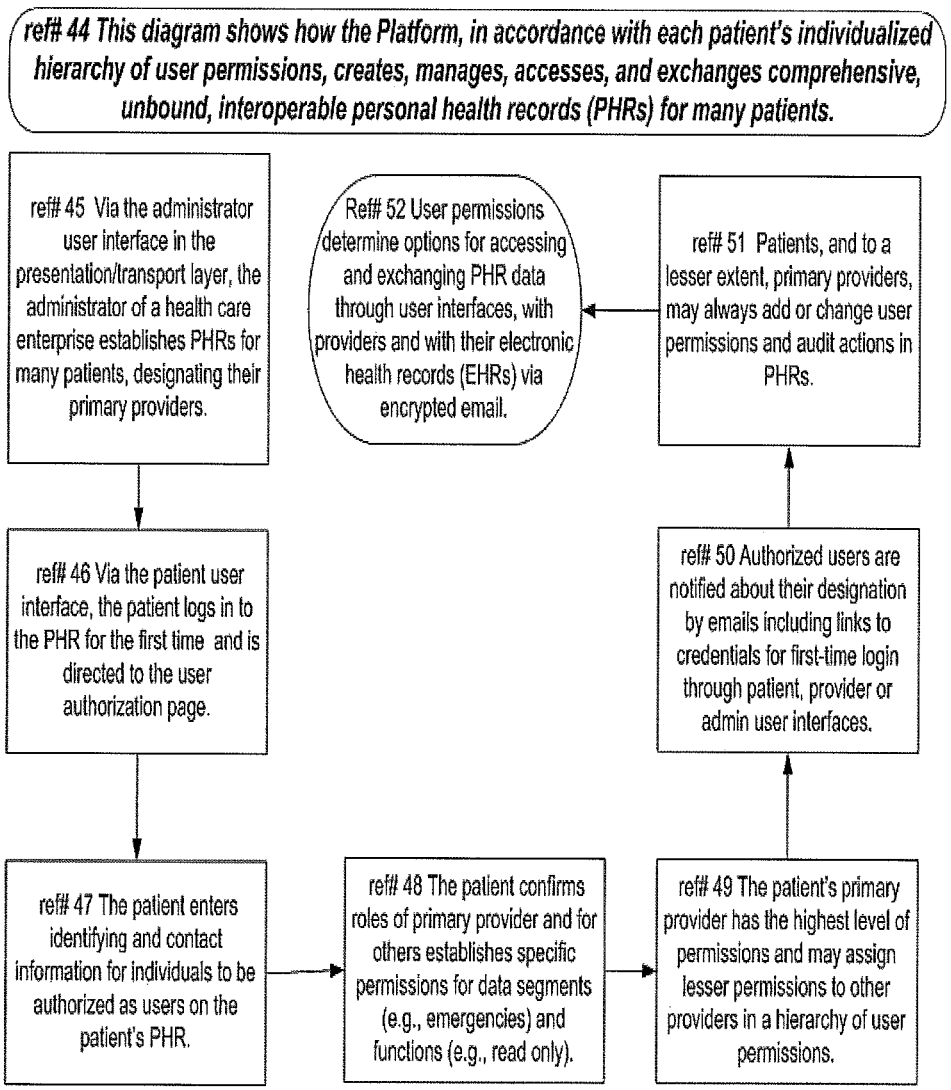
FIG. 8 is a block diagram showing how the PHR Platform, in accordance with each patient's individualized hierarchy of user permissions, creates, manages, accesses, and exchanges personal health records (PHR) for many patients in a health care enterprise.
Figure 9:
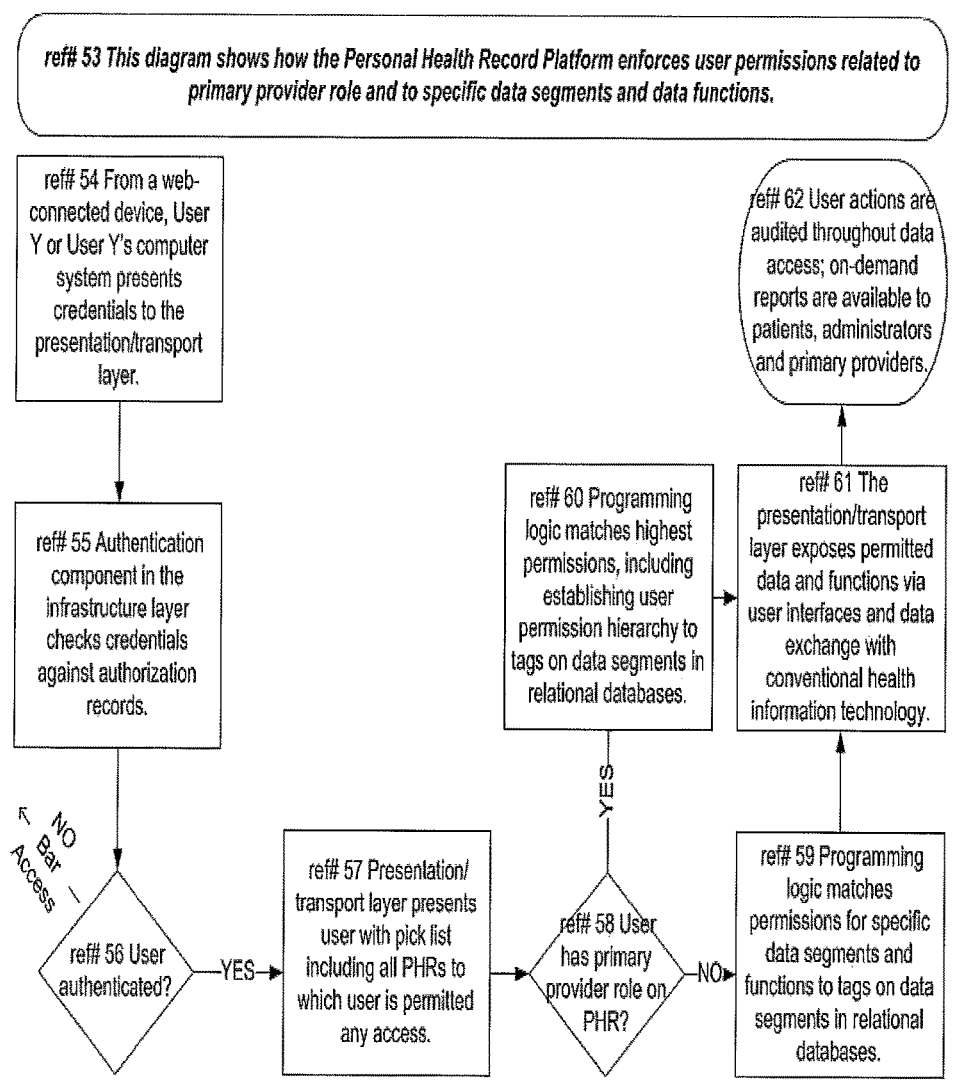
FIG. 9 is a block diagram showing how the personal health record (PHR) Platform enforces user permissions related to primary provider role and to specific data segments and data functions.

FIG. 7 shows how the PHR Platform creates, manages, accesses and exchanges a personal health record (PHR) for one patient in accordance with the patient's individualized hierarchy of user permissions (ref#35) as follows. A patient signs up for a PHR and establishes credentials for logging in via the patient user interface in the presentation/transport layer (ref#36). Via the patient user interface, the patient logs in to the PHR for the first time and is directed to the user authorization page (ref#37). The patient enters identifying and contact information for individuals to be authorized as users on the patient's PHR (ref#38). The patient gives users roles (e.g., account admin, primary provider) or establishes specific permissions for data segments (e.g., emergencies) and functions (e.g., read only) (ref#39). A user designated as primary provider has the highest level of permissions and may assign lesser permissions to other providers in a hierarchy of user permissions (ref#40). Authorized users are notified about their designation by emails including links to credentials for first-time login through patient or provider user interfaces (ref#41). Patients, and to a lesser extent, account administrators and primary providers, may always add or change user permissions and audit their actions in the PHR (ref#42). User permissions determine options for accessing and exchanging PHR data through user interfaces, with electronic health records (EHRs) and via web services (ref#43).

FIG. 8.

This diagram shows how the PHR Platform, in accordance with each patient's individualized hierarchy of user permissions, creates, manages, accesses and exchanges personal health records (PHRs) for many patients in a health care enterprise (ref#44), as follows. Via the administrator user interface in the presentation/transport layer, the enterprise establishes PHRs for many patients, designating their primary providers (ref#45). Via the patient user interface, the patient logs in to the PHR for the first time and is directed to the user authorization page (ref#46). The patient enters identifying and contact information for individuals to be authorized as users on the patient's PHR (ref#47). The patient confirms roles of primary provider and for others establishes specific permissions for data segments (e.g., emergencies) and functions (e.g., read only) (ref#48). The patient's primary provider has the highest level of permissions and may assign lesser permissions to other providers in a hierarchy of user permissions (ref#49). Authorized users are notified about their designation by emails including links to credentials for first-time login through patient, provider or admin user interfaces (ref#50). Patients, and to a lesser extent, enterprise administrators and primary providers may always add or change user permissions and audit their actions in the PHR (ref#51). User permissions determine options for accessing, updating (defined as entering new data) and exchanging PHR data through user interfaces, with electronic health records (EHRs) and via web services (ref#52). The PHR automatically recognizes and consolidates new with existing data elements so that appropriately authorized users may access and exchange comprehensive patient data (defined to include all data in a patient PHR) with other appropriately authorized users.

FIG. 9.

This diagram shows how the PHR Platform enforces user permissions related to primary provider role and to data segments and data functions (ref#53) as follows. From a web-connected device, User Y or User Y's computer system presents credentials to the presentation/transport layer of the PHR Platform (ref#54). An authentication component in the infrastructure layer checks credentials against authorization records (ref#55). If the user is not authenticated, the Platform denies further access (ref#56). If the user is authenticated (ref#56), the presentation/transport layer presents users with a pick list including all the PHRs to which the user is permitted any access (ref#57). The selected user may, or may not, have a primary provider role on the PHR (ref#58). If the selected user has the primary provider role, then programming logic matches the highest level of permissions, including establishment of a user permission hierarchy to tags on data segments in relational databases (ref#60). If the selected user does not have the primary provider role on the PHR, the programming logic matches permissions for specific data segments and functions to tags on data segments in relational databases (ref#59). The presentation/transport layer decrypts/exposes permitted data and functions through user interfaces, EHR and web services data exchanges (ref#61). User actions are audited throughout data access; on-demand receipts are available to patients, administrators and primary providers (ref#60).

What I claim is:

1. A non-transitory computer readable media comprising computer executable instructions to perform a method for creating, managing, accessing, updating and exchanging electronic personal health record(s) ("PHR"s) of multiple patients in accordance with their individualized hierarchies of user permissions using a web-based PHR software platform containing a plurality of N layers including at least an infrastructure layer comprising relational databases in which all of the personal health records of the patients is received as incoming data and stored in the relational databases with the web-based PHR software platform including programming logic; a data layer; an application layer containing business rules controlling communication between the layers of the software platform and containing data representative of government regulations and practice guidelines relative to PHR patient care; and a presentation/transport layer which provides user interfaces to access, transmit and exchange personal health records of patients to and from the software platform; said method comprising the steps of:

(a) storing data segments representative of at least one of physical health, mental health, conditions, referrals, medications, substance abuse, allergies, procedures, and care plans of the patients at the data layer and identifying a plurality of data functions for each of the data segments at the data layer;

(b) embedding in the application layer individualized patient hierarchies of user permissions governing the hierarchy of disclosure to stored data of each patient such that patients have the greatest access to patient data and patient hierarchies, individuals authorized by patients as providers have lesser access, and other individuals granted user access by the authorized providers have the least access;

(c) using the programming logic for tagging stored patient PHR data in the relational databases with information to identify data segments and data functions with user permissions granted to authorized users by each patient, wherein the tags identifying user permissions of each authorized user on each of the data segments are stored in encrypted form in the relational databases and decrypted in the presentation/transport layer to expose permitted data and functions to authorized users through user interfaces, EHR and web services data exchange;

(d) using the programming logic to correlate tagged patient PHR data and data functions with the individualized patient hierarchies of user permissions defined in step (b);

(e) authenticating users who identify themselves in the presentation/transport layer from web-connected devices;

(f) using the programming logic to control the disclosure of data to and from the software platform by matching an authenticated user to the user permissions specified in the tagged data for performing specified data functions;

(g) filtering the matching operation in step (f) such that unmatched data and unmatched data functions are filtered out and not presented via user interfaces to authorized users for any use thereof;

(h) scanning data in the data layer and/or the application layer to locate gaps in patient care and the presence of gaps based on non-compliance with the government regulations and practice guidelines in the presentation/transport layer; and (i) creating an alert in response to the detection of gap(s) for notifying providers of the existence of gap(s) and communicating the alert to a mobile device of one or more users with suitable permissions to receive such alerts.

2. The non-transitory computer readable media of claim 1 wherein the presentation/transport layer enables authenticated users, in accordance with individualized hierarchies of user permissions in the application layer, to access patient PHRs via user interfaces provided by the presentation/transport layer appropriate to users who identify themselves in the presentation/transport layer.

3. The non-transitory computer readable media of claim 1 wherein the presentation/transport layer enables authenticated users, in accordance with individualized hierarchies of user permissions in the application layer, to exchange data in patient PHRs from the infrastructure layer with external electronic health record systems (EHRs).

4. The non-transitory computer readable media of claim 3 wherein the presentation/transport layer enables the exchange of such data in patient PHRs with external electronic health record systems (EHRs) or external computer information systems to occur via web services.

5. The non-transitory computer readable media of claim 1 wherein the infrastructure layer contains cryptography which permits the presentation/transport layer to enable authenticated users, in accordance with individualized hierarchies of user permissions in the application layer, to use encryption and decryption for sending and receiving e-mail messages which include patient data and documents as attachments thereto.

6. The non-transitory computer readable media of claim 1 wherein the programming logic in the infrastructure layer scans for gaps in patient care in each of the data and application layers to alert authorized users of the presence of such gaps and to escalate such notification until gap remediation occurs.

7. The non-transitory computer readable media of claim 6 wherein alerts to users about the presence of a gap in patient care includes a menu of choices for resolving the specific gap.

8. The non-transitory computer readable media of claim 7 wherein users who receive alerts about the presence of a gap in patient care are repeatedly prompted by email and text messages to select a menu item and provide details about the menu item for resolving the specific gap, to indicate when they have implemented a particular method of gap resolution, and, to describe the results of gap resolution including obstacles.

9. The non-transitory computer readable media of claim 8 wherein users who receive alerts about the presence of a gap in patient care related to practice guidelines or regulatory compliance, after being prompted by email and text messages to select and provide details about a menu item for resolving a specific gap, may indicate that they will select a strategy not included in menu items and may justify their exception to practice guidelines or regulatory compliance.

10. The non-transitory computer readable media of claim 9 wherein after a predetermined brief time period, alerts are forwarded to supervisory personnel who oversee clinical care of patients when users fail to respond to alerts about the presence of gaps in patient care, fail to select menu items for resolving those gaps, fail to indicate when they have implemented particular methods of gap resolution, or fail to describe the results of gap resolution including obstacles.

11. The non-transitory computer readable media of claim 1 wherein programming logic in the infrastructure layer tags data stored in the relational databases, identifying patient owners of data, data segments, and associations of data segments with the individualized of user permissions so that only permitted data are disclosed to users through the presentation/transport layer.

12. The non-transitory computer readable media of claim 11 wherein the programming logic in the infrastructure layer tags data stored in relational databases, identifying patient owners of data, data segments, and association of data segments with individualized hierarchies of user permissions so that authorized users, can only forward data made accessible to the authorized user as permitted data through the presentation/transport layer to other users identified in the PHR data as authorized users.

13. The non-transitory computer readable media of claim 1 wherein the tagged data is continuously audited for documenting disclosures of patient data in audit logs accessible to patients and to other appropriately authorized users.

14. The non-transitory computer readable media of claim 13 wherein continuous auditing automatically documents provider compliance with practice guidelines and regulatory requirements, allowing providers to make and justify exceptions to compliance.

15. The non-transitory computer readable media of claim 1 wherein through a patient user interface provided by the presentation/transport layer, patients authorize primary providers with the highest level of permissions to grant other individuals user(s) authorized access at lower levels of permissions in the hierarchies of user permissions.

16. The non-transitory computer readable media of claim 15 wherein through the provider user interface, primary providers can grant and manage lesser permissions for other, secondary providers, in accordance with individualized patient user permission hierarchies, during referrals and care transitions and for purposes of care coordination.

* * * * *